(12) United States Patent
Taylor et al.

(10) Patent No.: US 9,993,147 B2
(45) Date of Patent: Jun. 12, 2018

(54) VAGINAL MANIPULATOR HAVING A DOOR WITH AN INCLINED SURFACE

(71) Applicant: Coloplast A/S, Humlebaek (DK)

(72) Inventors: Jeffrey Brian Taylor, Forest Lake, MN (US); Allen Gaynor, Coon Rapids, MN (US)

(73) Assignee: Coloplast A/S, Humlebaek (DK)

( * ) Notice: Subject to any disclaimer, the term of this patent is extended or adjusted under 35 U.S.C. 154(b) by 970 days.

(21) Appl. No.: 14/321,844

(22) Filed: Jul. 2, 2014

(65) Prior Publication Data

US 2014/0316208 A1    Oct. 23, 2014

Related U.S. Application Data

(63) Continuation of application No. 13/907,990, filed on Jun. 3, 2013, now Pat. No. 8,821,393.

(30) Foreign Application Priority Data

Sep. 17, 2012   (DK) .................................. 2012 70574

(51) Int. Cl.
*A61B 1/303*     (2006.01)
*A61B 1/32*      (2006.01)
(Continued)

(52) U.S. Cl.
CPC ................ *A61B 1/303* (2013.01); *A61B 1/32* (2013.01); *A61B 17/0218* (2013.01);
(Continued)

(58) Field of Classification Search
CPC ........... A61B 1/303; A61B 1/32; A61B 17/42; A61B 17/4241; A61B 17/0206;
(Continued)

(56) References Cited

U.S. PATENT DOCUMENTS 7,070,561 B1    7/2006  Ansari
7,087,055 B2 *  8/2006  Lim ..................... A61B 17/025
                                                606/198

(Continued)

FOREIGN PATENT DOCUMENTS

WO         03077770 A1    9/2003
WO       2005055819 A1    6/2005

*Primary Examiner* — Christian Sevilla
*Assistant Examiner* — Tracy Kamikawa
(74) *Attorney, Agent, or Firm* — Coloplast Corp., Coloplast A/S; Nick Baumann

(57) ABSTRACT

A vaginal manipulator includes a shaft, a head, and a door. The head has an anterior side opposite a posterior side and includes a core fixed to the shaft and a sleeve coupled in a sliding relationship to the core. The door has a distal end that is hinged to the sleeve and a proximal end that is movable away from the core of the head. A proximal end of the core defines a proximal end of the head and a distal end of the sleeve defines a distal end of the head, and the proximal end of the core is fixed to the shaft. The core includes a ramp and a recess that is sized to receive a portion of the door, and the door includes an inclined surface that is formed such that the distal end of the door is thinner than the proximal end of the door.

12 Claims, 13 Drawing Sheets

Related U.S. Application Data

(60) Provisional application No. 61/702,254, filed on Sep. 18, 2012.

(51) Int. Cl.
  *A61B 17/02*  (2006.01)
  *A61B 17/42*  (2006.01)
  A61B 17/00  (2006.01)
  A61B 90/00  (2016.01)

(52) U.S. Cl.
  CPC .... *A61B 17/42* (2013.01); *A61B 2017/00849* (2013.01); *A61B 2017/00991* (2013.01); *A61B 2090/061* (2016.02)

(58) Field of Classification Search
  CPC ............ A61B 17/0218; A61B 17/0281; A61B 5/4325; A61B 5/4337; A61B 2017/4216; A61B 2017/4225
  See application file for complete search history.

(56) References Cited

U.S. PATENT DOCUMENTS

| | | |
|---|---|---|
| 2007/0038216 A1 | 2/2007 | Hamada |
| 2011/0034776 A1 | 2/2011 | Dixon et al. |
| 2012/0157761 A1 | 6/2012 | Crank et al. |

* cited by examiner

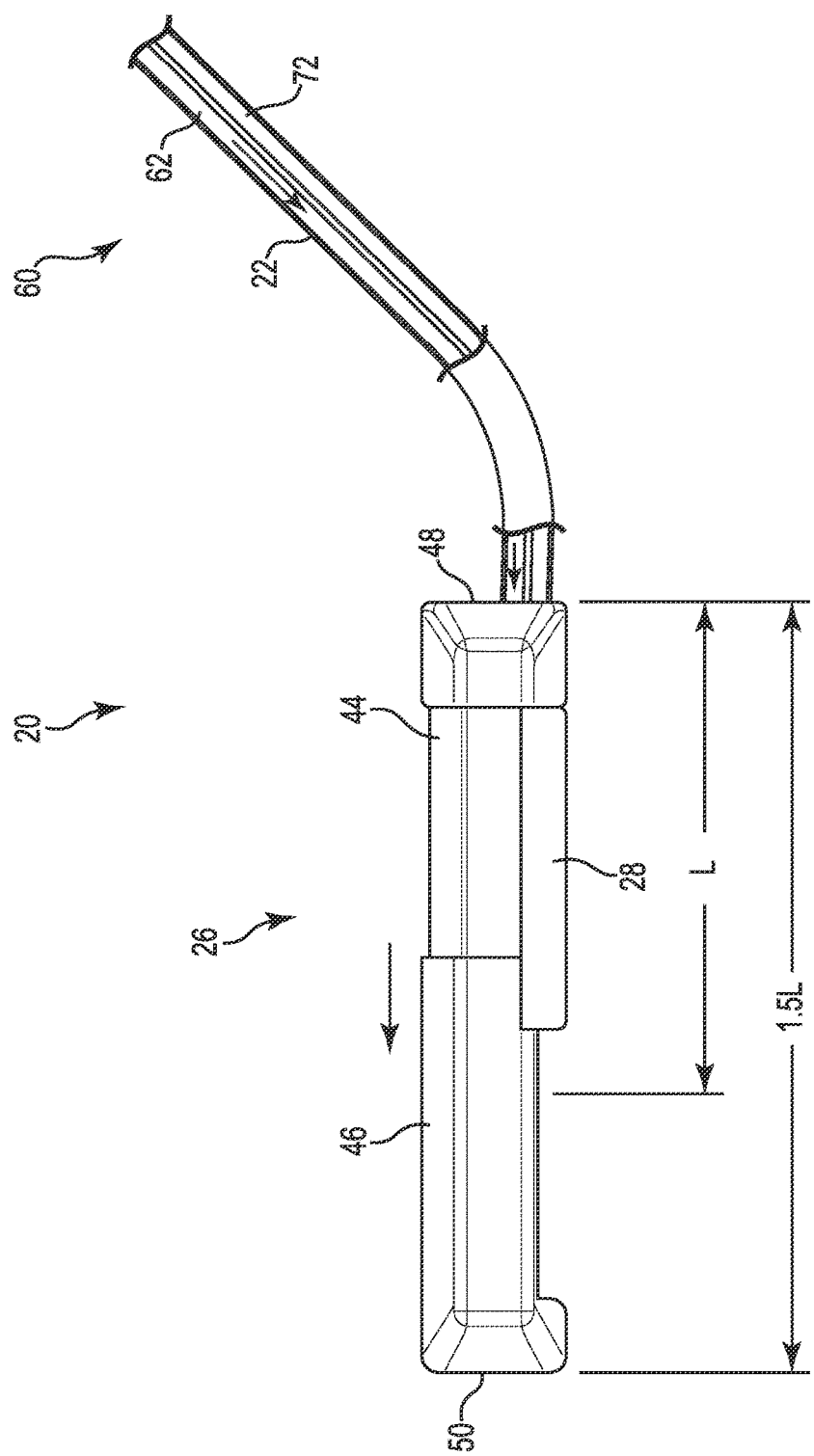

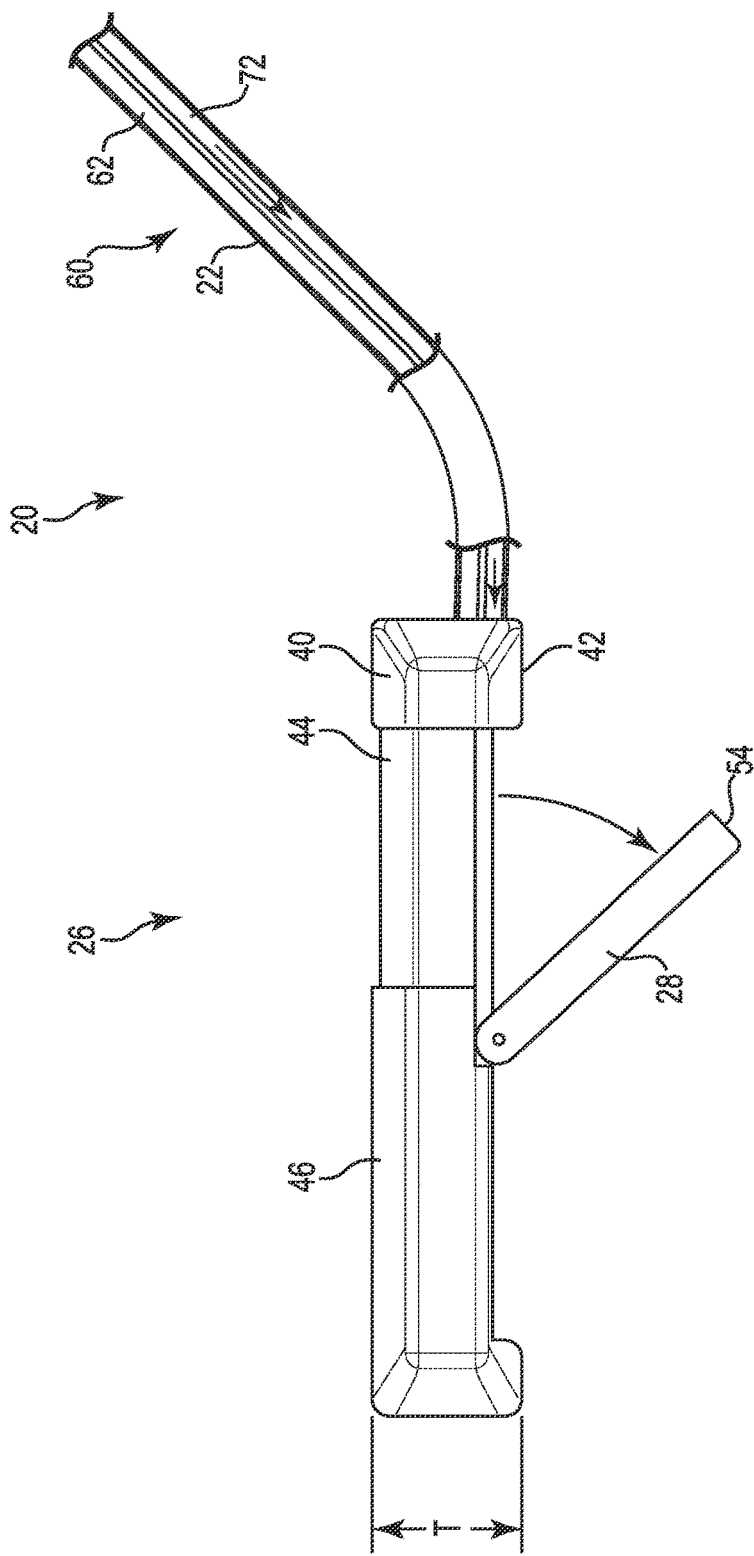

VAGINAL MANIPULATOR HAVING A DOOR WITH AN INCLINED SURFACE

CROSS-REFERENCE TO RELATED APPLICATIONS

This application is a continuation of U.S. patent application Ser. No. 13/907,990, filed Jun. 3, 2013, now U.S. Pat. No. 8,821,393, which claims the benefit of U.S. Provisional Application No. 61/702,254, filed Sep. 18, 2012.

BACKGROUND

There is a trend to move toward minimally invasive surgical procedures that allow the patient to recover faster. Faster recoveries are associated with less time in post anesthesia and other care units, which can translate to a lower cost of patient care.

Many such minimally invasive surgical procedures are performed laparoscopically through multiple access ports formed in the abdomen (e.g., a trans-abdominal approach). At least one access port is formed to provide access for a camera that allows visualization of the internal organs, and at least one access port is formed to provide surgical tools with access to the internal organs. However, it is often the case that the organ selected for surgical intervention will have a surface that is oriented away from the camera such that the surgeon has an imperfect view of the complete organ.

Surgeons would welcome a new device for manipulating the orientation of internal organs to provide a better view and access to all surfaces of the organ.

SUMMARY

One aspect provides a vaginal manipulator including a shaft attached to a head and a door connected to the head. The head has an anterior side opposite a posterior side and includes a core fixed to the shaft and a sleeve coupled in a sliding relationship to the core. The door is coupled to the core and is movable relative to the posterior side of the head through an opening provided in the sleeve. A proximal end of the core defines a proximal end of the head and a distal end of the sleeve defines a distal end of the head. The proximal end of the core is fixed to the shaft. The sleeve moves relative to the core to provide the head with an adjustable length between the proximal end of the head and the distal end of the head.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 3A is a side view of the head illustrated in FIG. 1 in an extended or lengthened state.

FIG. 3B is a side view of the head illustrated in FIG. 3A with the door "kicked-out" into an extended state.

DETAILED DESCRIPTION

Figure 1:
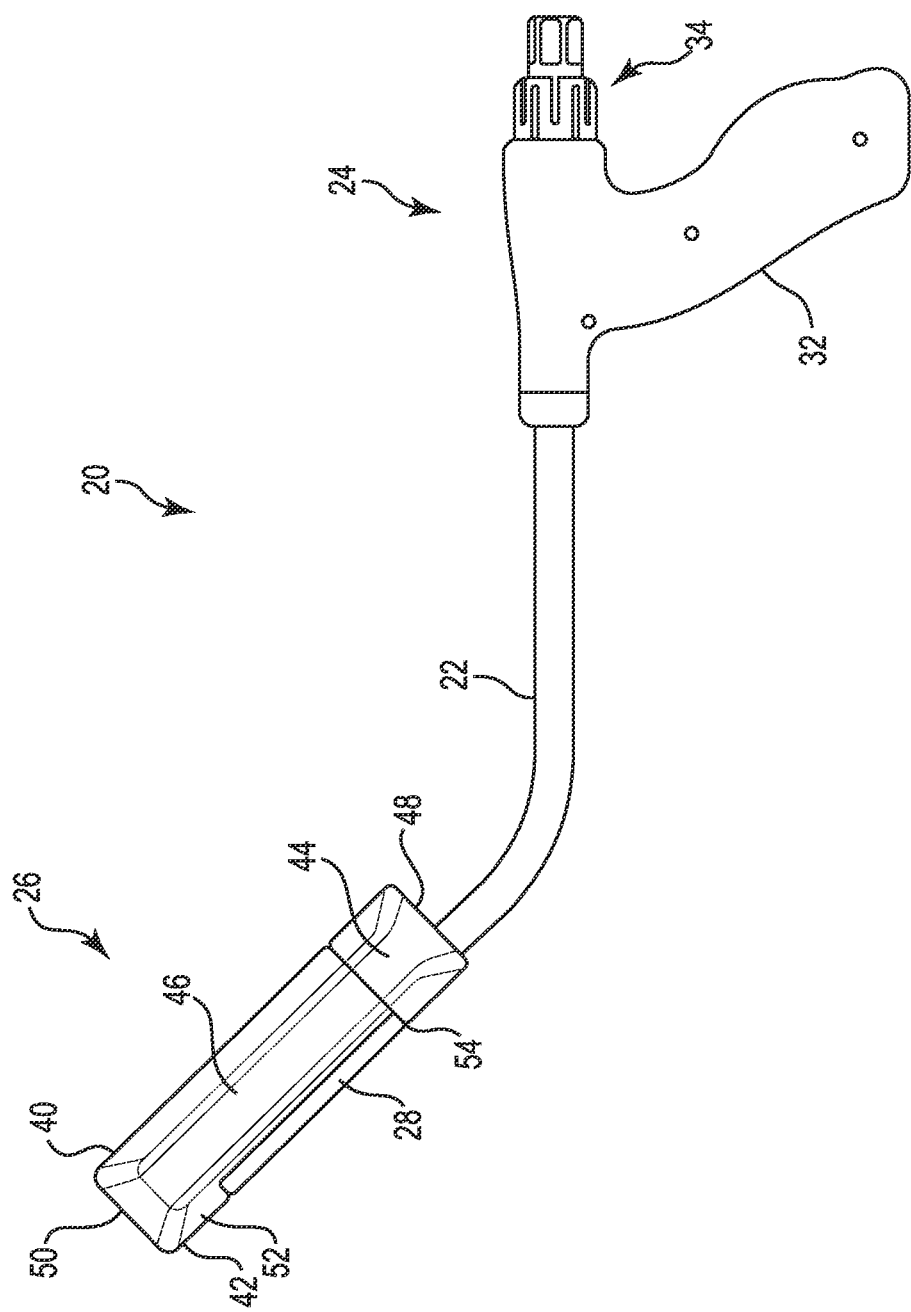
FIG. 1 is a side view of one embodiment of a vaginal manipulator including an adjustable length head and a posterior kick-out door.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Tissue includes soft tissue, which includes dermal tissue, sub-dermal tissue, ligaments, tendons, or membranes. As employed in this specification, the term "tissue" does not include bone.

Anterior means "forward" or "front," and posterior means "rearward" or "back" relative to the patient. For example, relative to surfaces of an organ in the human body, an anterior side is oriented forward toward the belly and a posterior side is oriented rearward toward the spine.

Individuals have anatomy of different sizes. For example as regards females, the vaginal vault can vary in length (depth). Some women having had a hysterectomy will have all or some of the cervix removed (e.g., a cervical stump is at times left in place at the apex of the vagina). Embodiments provide a surgical device having a head that is useful in manipulating walls of the vagina and portions of the cervix (if present). The head includes a door (or a kick-out door) that can be deployed to move a posterior wall of the vagina into a line of sight of a surgeon during a laparoscopic procedure. The device includes an adjustable length head that is operable to provide improved manipulation and control of the apex the vagina, no matter the size of the individual.

The surgical device is useful in gynecological, colorectal and other procedures. The surgical device may be manually deployed into an organ during an open procedure. The surgical device may be employed in a laparoscopic procedure or robotically manipulated in a robotically-assisted surgical procedure.

For example, in a laparoscopic procedure a camera system is inserted into a camera port formed through the wall of the abdomen to allow visualization of the internal organs. Other ports are formed in the abdomen to allow tools and devices to access a selected organ. The selected organ will have a surface oriented toward the camera (an anterior side) and a surface away from the camera (a posterior side). The head of the surgical device is provided with a movable surface that operates to present or displace the posterior side of the selected organ in a direction for improved visualization by the camera. This feature is particularly useful when manipulating a posterior wall of the vagina that is typically oriented to face away from the abdomen and away from a camera that is inserted into the abdomen laparoscopically.

FIG. 1 is a side view of one embodiment of a vaginal manipulator 20. The vaginal manipulator 20 (manipulator 20) includes a shaft 22 connected between a handle 24 and a head 26, and a door 28 coupled to the head 26. The head 26 is configured to provide an adjustable length and can be lengthened or shortened as desired by the surgeon. The door 28 is movable away from the head 26 to allow the surgeon to manipulate a posterior wall of the vagina for improved viewing and access during surgery.

In one embodiment, the shaft 22 is a rigid shaft formed from a metal tube, such as stainless steel tube. In one embodiment, the shaft 22 is substantially straight and is provided without a bend along its length. In one embodiment, the shaft 22 is curved to include a bend as illustrated in FIG. 1 having an angle in the range from about 5-90 degrees, with one acceptable angle being about 45 degrees. In one embodiment, the shaft 22 is curved such that a top side (or anterior side) of the head 26 is closer to the handle 24 than a bottom side (or posterior side) of the head 26 is to the handle 24. The curved shaft 22 is adapted to orient the vagina in its natural location for a patient in surgery while at the same time orienting the handle 24 in a comparable position for manipulation by the surgeon.

The shaft 22 is designed to carry loads and bending forces of less than 20 pounds. In one embodiment, the rigid shaft 22 is fabricated to plastically deform (fail) at a bending force of 20 pounds. The shaft 22 is designed to noticeably deform/fail when the bending force is greater than 20 pounds. This feature allows the manipulator 20 to move/orient the vagina during surgery while preventing the operating room staff from unintentionally delivering an undesirably large force to the patient during surgery.

The shaft 22 encloses portions of the actuator 34 that extend from the handle 24 to the head 26. In some applications, it is desirable that the shaft 22 is rigid to allow the surgeon to have a one-to-one correlation between movement of the handle 24 and movement of the head 26. In addition, a rigid shaft 22 allows the surgeon to use the manipulator 20 as a lever in moving tissue or in adjusting a location of an organ within the body.

The embodiment illustrated in FIG. 1 provides one single rigid shaft 22 connected between the handle 24 and the head 26. In one embodiment, an overall length of the manipulator 20 from a leading end of the head 26 to a trailing end of the handle 24 is in a range between 12-15 inches, with one acceptable overall length for the device of about 13.8 inches (35 cm). The length of the manipulator 20 is thus suitably long enough to accommodate even obese patients. The sliding head 26 increases the length of the manipulator by a distance of between about 1-10 cm, and preferably by a distance of between about 2-6 cm.

The handle 24 includes a grip feature 32 and an actuator 34. The handle 24 provides a control surface or a grip for the surgeon (or assistant) to grab during use of the manipulator 20. The actuator 34 is connected with the door 28 to allow the surgeon to move the door 28 open/closed (out/in) relative to the head 26.

The handle 24 is a plastic or metal structure. In one embodiment, the handle 24 is provided as a two-piece structure that is fitted in a mating arrangement around the shaft 22 and portions of the actuator 34. The grip feature 32 is elongated to provide a surface that the surgeon may grasp during retroversion of the vagina or other organ.

The actuator 34 operates to adjust the length of the head 26 and to move the door 28 and can include a knob or a sliding feature that is suitably connected with a linkage attached to the head 26 and the door 28. One suitable actuator 34 assembly is described below with reference to FIG. 2 and includes a mechanism that converts rotational movement of the actuator 34 into a sliding movement of a portion of the head 26 along with deployment of the door 28 relative to the head 26.

The head 26 has an anterior side 40 opposite a posterior side 42 and includes a core 44 that is fixed to the shaft 22 and a sleeve 46 that is coupled in a sliding relationship to the core 44. In one embodiment, a proximal end 48 of the core 44 defines a proximal end of the head 26 and a distal end 50 of the sleeve 46 defines a distal end of the head 26. The proximal end 48 of the core 44 is fixed to the shaft 22. As described below, the door 28 is hinged to the head 26 such that a proximal end 54 of the door 28 is movable away from a posterior side 42 of the head 26.

The head 26 is suitably fabricated from plastic or metal. Suitable plastic materials for fabricating the head 26 include polycarbonate, acrylonitrile-butadiene-stryrene (ABS), acetal resin, or polysulfone as examples.

The manipulator 20 is useful in gynecological, colorectal and other procedures. The manipulator 20 may be manually deployed into an organ during an open procedure, or the head 26 may be employed in a laparoscopic procedure or robotically manipulated in a robotically-assisted surgical procedure.

For example, in a laparoscopic procedure a camera system is inserted into a camera port formed through the wall of the abdomen to allow visualization of the internal organs. Other ports are formed in the abdomen to allow tools and devices to access a selected organ. The selected organ will have a surface oriented toward the camera (an anterior surface) and a surface away from the camera (a posterior surface). The head 26 is operable to move/manipulate the anterior surface of the selected organ. In addition, the door 28 is operable to present or displace the posterior surface of the organ in a direction for improved visualization by the camera. This feature is particularly useful when manipulating a posterior wall of the vagina that is typically oriented to face away from the abdomen and away from a camera that is inserted into the abdomen laparoscopically.

Figure 2:
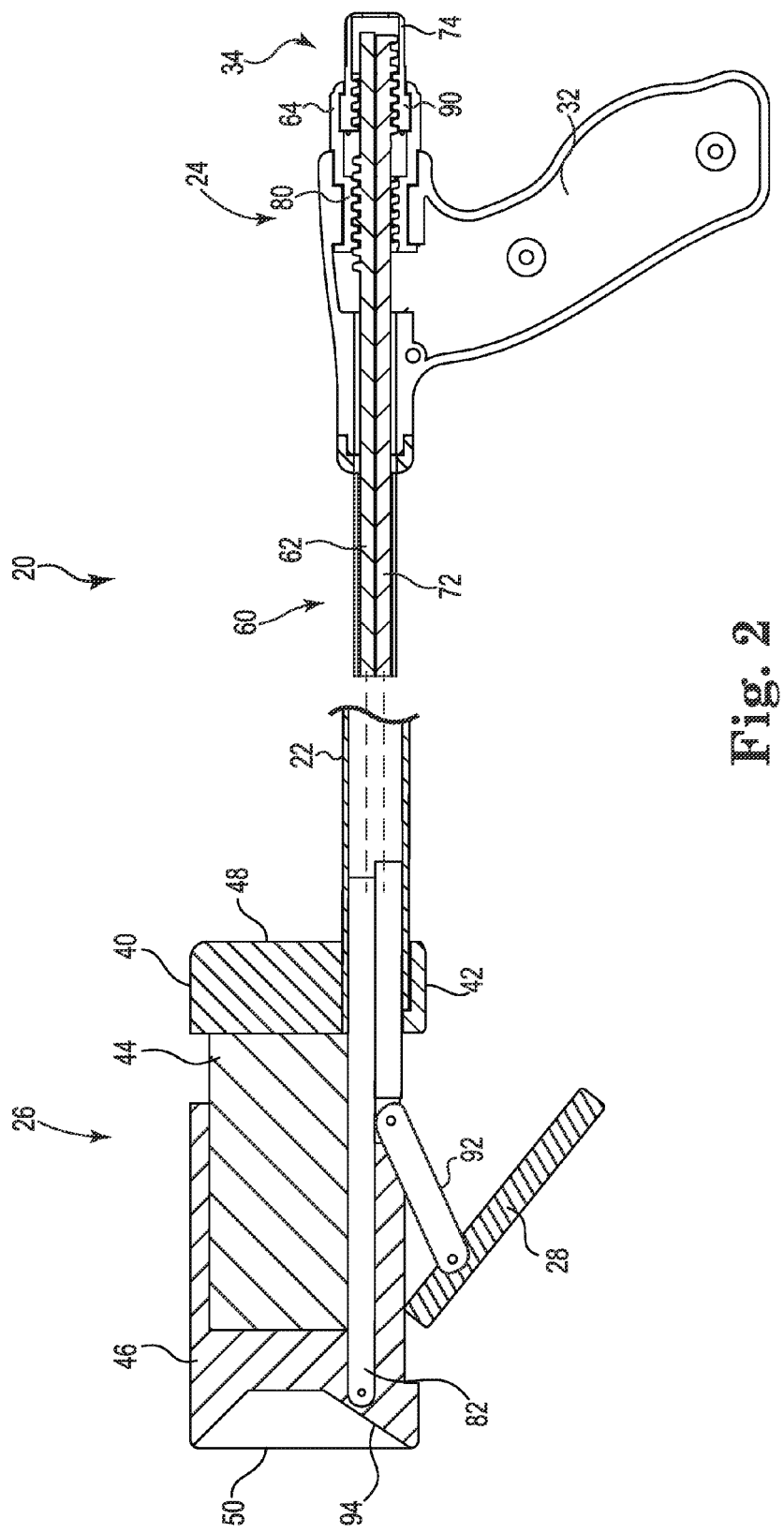
FIG. 2 is a partial cross-sectional view of the vaginal manipulator illustrated in FIG. 1.

FIG. 2 is a partial cross-sectional view of the manipulator 20.

The actuator 34 is connected to a movement mechanism 60 that is retained within the shaft 22 and extends from the handle 24 to the head 26. In one embodiment, the movement mechanism 60 is provided as a split rod having a first rod section 62 coupled between a first knob 64 of the actuator 34 and the sleeve 46 of the head 26, and a second rod section 72 coupled between a second knob 74 of the actuator 34 and the door 28 of the head 26.

In the exemplary illustrated embodiment, the first rod section 62 is connected to the first knob 64 of the actuator 34 by a thread 80 and to the sleeve 46 of the head 26 by a link 82. The second rod section 72 is connected to the second knob 74 of the actuator 34 by a thread 90 and to the door 60 of the head 26 by a link 92.

In one embodiment, rotational movement of the first knob 64 displaces the first rod section 62 to move the sleeve 46 outward (distally) or inward (proximally) relative to the core 44. In one embodiment, rotational movement of the second knob 74 displaces the second rod section 72 to move the door 28 relative to the posterior surface 42 of the head 26. The links 82, 92 thus allow the length extending sleeve 46 and the door 28 to move independently of the core 44.

In one embodiment, the movement mechanism 60 is configured to displace the sleeve 46 or the door 28 in proportion to the movement of the knobs 64, 74, respectively. In one example, the threads 80, 90 are provided as worm gears that displace each of the respective rods 62, 72, respectively, an incremental distance based upon the movement of the knobs 64, 74. In this manner, the movement mechanism 60 is operable to move the sleeve 46 to a selected axial position relative to the core 44. In one embodiment, the movement mechanism 60 is operable to "lock" the sleeve 46 in a selected axial position relative to the core 44.

In one embodiment, the distal end 50 of the sleeve 46 is formed to include a pocket 94 that is configured to receive a fornix of the cervix of the vagina.

FIG. 3A and FIG. 3B are side views of the head 26 with the sleeve 46 in an extended or lengthened state. The movement mechanism 60 is operable to move the sleeve and the door 28 sequentially, or alternatively, at the same time.

FIG. 3A illustrates the first rod section 62 moved within the shaft 22 in a distal direction to extend the sleeve 46 in a distal direction away from the core 44. In one embodiment, the head 26 is provided with a compacted head length L when the sleeve 46 is located in the most proximal position. The movement mechanism 60 operates to extend the sleeve 46 to provide the head 26 with an extended head length of about 1.5 L.

In one embodiment, the core 44 provides a first anterior side portion (i.e., exposed in FIG. 3A) of the head 26 and the sleeve 46 provides a second anterior side portion of the head 26, such that when the distal end 50 of the sleeve 46 is moved away from the proximal end 48 of the core 44, an effective length of the anterior side of the head 26 is expanded or increased.

FIG. 3B illustrates the second rod section 72 moved within the shaft 22 in a distal direction to rotate the proximal end 54 of the door 28 away from the posterior side 42 of the head 26. In this manner, the "kick out" door 28 is operable to displace a posterior wall of the vagina into a line of sight of the surgeon during a laparoscopic procedure.

In one embodiment, the head 26 has a head width extending between parallel lateral sides of the head (e.g., extending into the paper of the illustration) and a head thickness T (FIG. 3B) extending between the anterior side 40 and the posterior side of the head 42, and the head width is greater than the head thickness T.

In one embodiment, the head 26 is provided with a lubricating coating that allows the head 26 to have reduced friction for placement into the vagina. One suitable lubricating coating is a hydrophilic coating available as the HARMONY™ Advanced Hydrophilic Coating available from SurModics, Inc., Eden Prairie, Minn.

Figure 4A:
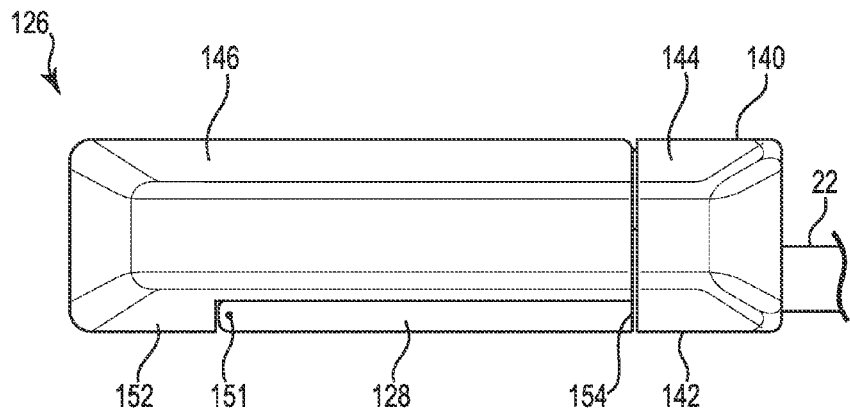
FIG. 4A is a side view of one embodiment of a vaginal manipulator head.
Figure 4B:
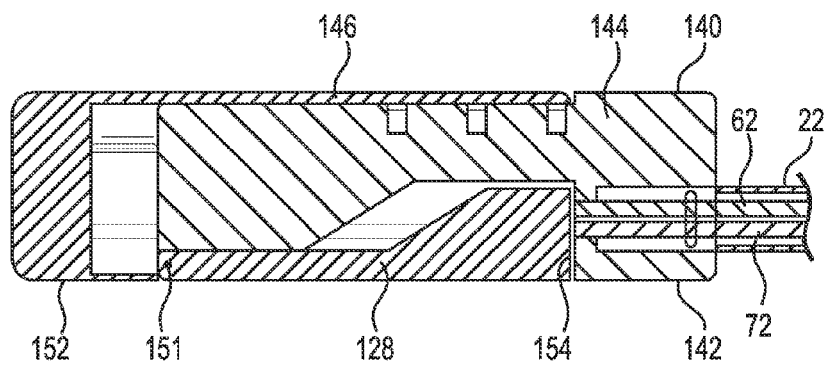
FIG. 4B is a cross-sectional view of the head illustrated in FIG. 4A.
Figure 4C:
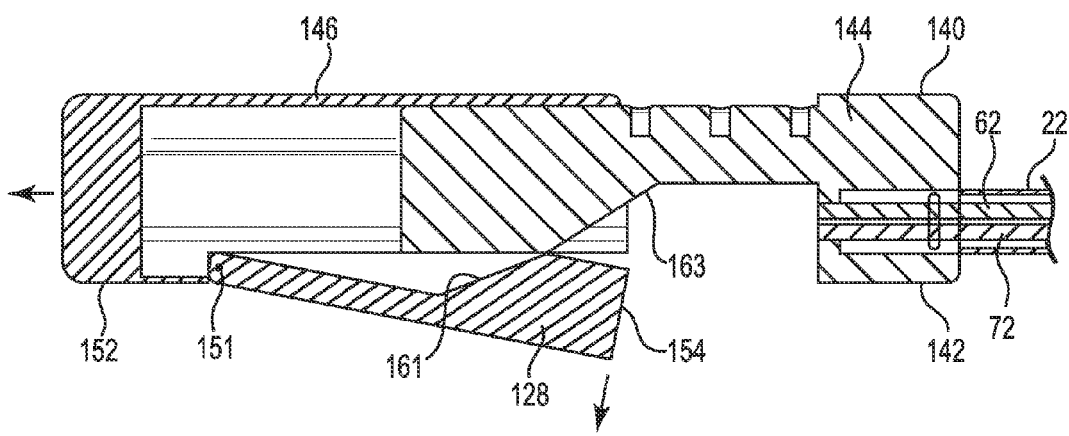
FIG. 4C is a cross-sectional view of the head illustrated in FIG. 4A with the head in an extended or lengthened state and the door "kicked-out" into an extended state.

FIG. 4A is a side view of one embodiment of a vaginal manipulator head 126, and FIGS. 4B and 4C are cross-sectional views of the head 126 with a door 128 "kicked-out" into an extended state.

The head 126 has an anterior side 140 opposite of a posterior side 142. The head 126 includes a core 144 fixed to the shaft 22 described above and a sleeve 146 that is coupled in a sliding relationship to the core 144. A door 128 is provided having a distal end 151 that is hinged to the sleeve 146. In one embodiment, the door 128 is configured to kick out away from a posterior surface 142 of the head 126 when the sleeve 146 is moved in a distal direction relative to the core 144.

With reference to FIGS. 4B and 4C, one embodiment of the door 128 includes an inclined surface 161 that cooperates with a ramp 163 formed on the core 144. Movement of the sleeve 146 in a distal direction rotates the door 128 away from the posterior side 142 of the head 126. For example, movement of the sleeve 146 in a distal direction causes the inclined surface 161 to slide along the ramp 163 and move a proximal end 154 of the door 128 away from the posterior side 142 of the head 126. The sleeve 146 is moved by the movement of the first rod section 62, in a manner similar to that described above.

In one embodiment, the door 128 is coupled to the sleeve 146 and moves when the sleeve 146 moves. In one embodiment, the door 128 is coupled to the second rod section 72 and can be move independently of movement of the sleeve 146. The coupling between the first and second rod sections 62, 72 and the sleeve 146 and the door 128 is not illustrated in FIGS. 4B-4C, but it is to be understood that one suitable coupling is illustrated in FIG. 2 above.

Figure 5A:
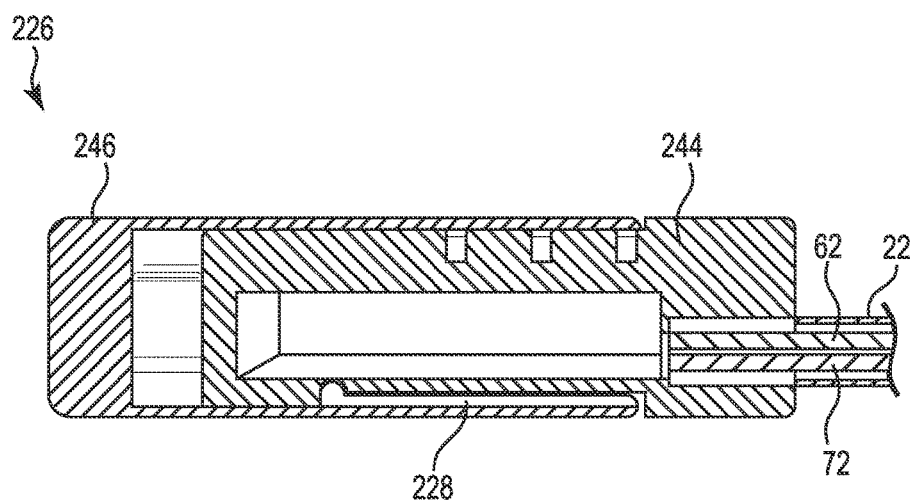
FIG. 5A is a cross-sectional view of one embodiment of a vaginal manipulator head including a door including a bias feature.
Figure 5B:
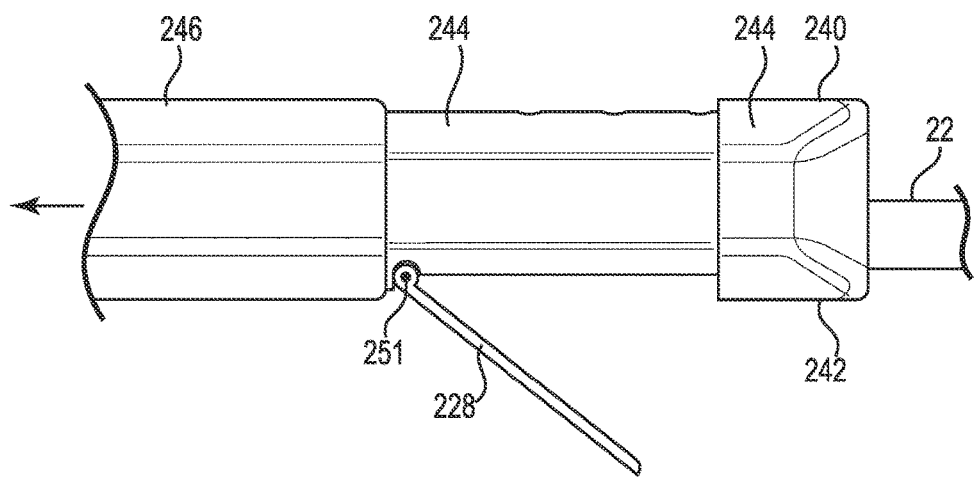
FIG. 5B is a side view of the head illustrated in FIG. 5A with the head in an extended or lengthened state and the door biased outward into an extended state.

FIG. 5A is a cross-sectional view and FIG. 5B is a side view of one embodiment of a vaginal manipulator head 226. The head 226 has an anterior surface 240 opposite a posterior surface 242 and includes a core 244 attached to the shaft 22 described above and a sleeve 246 that slides along the core 244. In one embodiment, the head 226 includes a door 228 that is coupled to the core 244 at a distal end 251 of the door by a torsion spring. Movement of the sleeve 246 in the distal direction allows the door 228 to release away from the core 244. In this embodiment, the door 228 automatically kicks out when the sleeve 246 is moved in the distal direction and the door 228 automatically is closed when the sleeve 246 is moved in the proximal direction. In an alternative embodiment, the door 228 is coupled to a movement mechanism similar to the movement mechanism 60 described above to allow the door 228 to move independently of the sleeve 246.

Figure 6A:
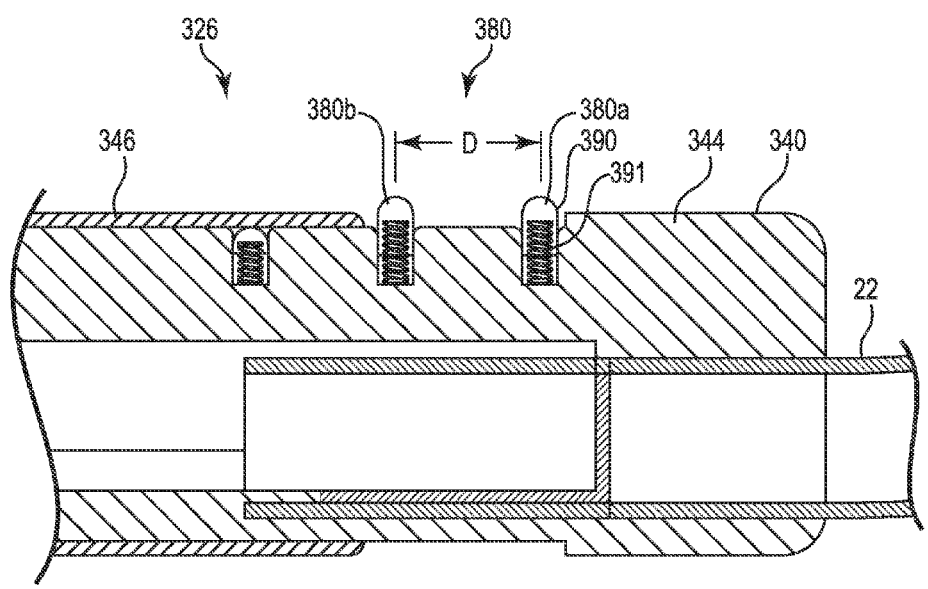
FIG. 6A is a cross-sectional view of one embodiment of a vaginal manipulator head including biased index features.
Figure 6B:
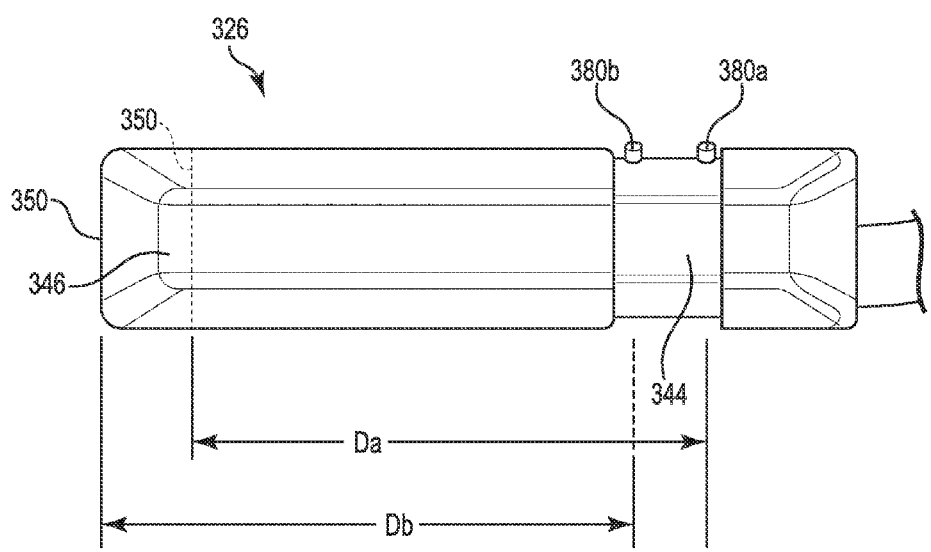
FIG. 6B is a side view of the head illustrated in FIG. 6A with the head in an extended or lengthened state and two index features biased out from an anterior surface of the head.

FIG. 6A is a cross-sectional view and FIG. 6B is a side view of one embodiment of a vaginal manipulator head 326 including biased index features 380. The index features 380 are configured to extend from a surface of the head 326 to contact an interior surface of the vagina, and in so doing, to be visible through the wall of the vagina. The surgeon, viewing the outer wall of the vagina trans-abdominally during a laparoscopic procedure is able to view and be guided by the index feature(s) 380.

For example, it is useful for a surgeon to be apprised of a location that is a specific distance away from the apex the vaginal vault, particularly when dissecting tissue from one or the other of the anterior or posterior surface of the exterior wall of the vagina. With this in mind, the head 326 is provided with index features 380 including a first index feature 380a and a second index feature 380b. Each of the index features 380 includes a smoothly rounded cap 390 and a bias element 391 that biases the cap 390 to project from the anterior side 340 of the head 326 when the sleeve 346 is moved out of the way in a proximal direction.

Each of the index features 380 is spaced a calculated distance D apart from a neighboring index feature (FIG. 6A), with a first one of the index features 380a located a known distance Da away from the proximal end 350 of the head 326. In this manner, the surgeon is informed that the proximal end 350 of the head 326 is a known distance (for example 5 cm) away from the first 380a index feature when the first 380a index features is initially biased upward in a projecting position. Subsequently, when the sleeve 346 is moved an additional distance in a proximal direction along the core 344, the second 380b index feature is biased to pop-up, and again indicate that the now extended proximal end 350 of the head 326 is a distance Db away from the second index feature 380b.

In one embodiment, each index feature 380 is configured to project from the anterior side 340 of the head 326 as the sleeve 346 is moved in a distal direction to expose the index feature 380. Movement of the sleeve 346 in the proximal direction will depress the index feature 380 and capture it under the sleeve 346. In one embodiment, the index feature 380 has a first position retained between the core 344 and the sleeve 346 and a second position in which the index feature 380 is biased to an extended position projecting away from the anterior side 340 of the head 326 when the sleeve 346 is moved away from the proximal end of the core 344.

In one embodiment, Da is equal to Db and each is about 5 cm. In one embodiment, Da is selected to be different than Db, and each is selected to indicate a desired and calculated distance from the leading end of the sleeve 346.

In one embodiment, the head is provided with a plurality of indexes 380 coupled to the core 344 and the indexes 380 are aligned (e.g., in a line) on a central longitudinal axis of the head 326.

FIGS. 7-12 are schematic views of the manipulator 20 employed to internally manipulate an orientation of the vagina V of the patient during a laparoscopic procedure. FIGS. 7-12 represent related anatomy but are not drawn to scale. The laparoscopic procedure may be of the robotically-assisted type of laparoscopic procedure. The manipulator is suited for manual use in dissecting tissues off of the vagina V and in manipulating the orientation of the vagina V. Although features of a laparoscopic vaginal procedure are described below, it is to be understood that the manipulator 20 is suitable for manually manipulating the vagina or other organs in other surgical procedures, including other robotic procedures and the like.

Figure 7:
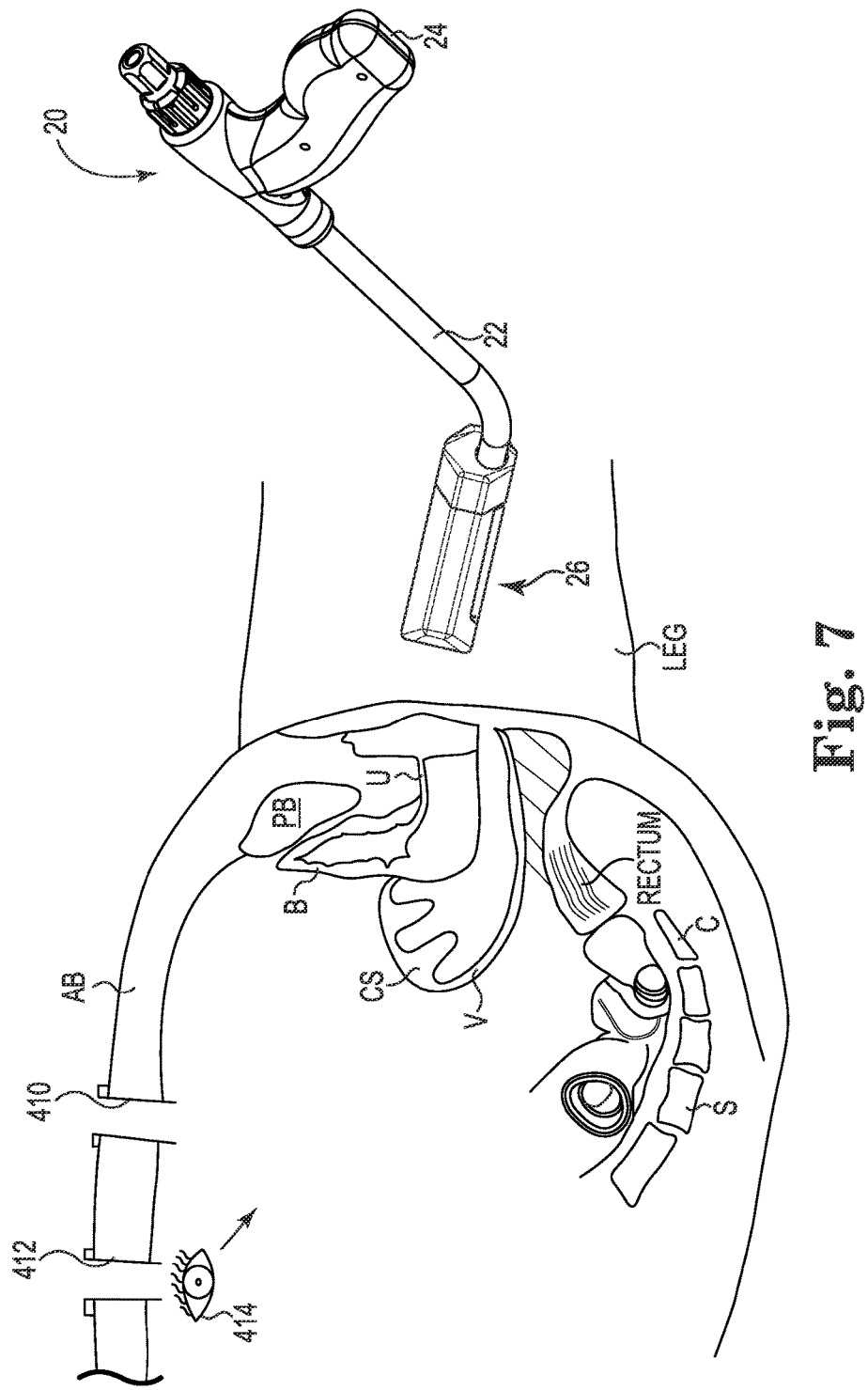
FIG. 7 is a schematic view of the vaginal manipulator illustrated in FIG. 1 employed in a laparoscopic surgical procedure.

FIG. 7 is a schematic view of internal organs of a supine patient with the head 26 of the manipulator 20 in position for insertion into the vagina V. A natural vagina has an entrance and terminates at the cervix, which communicates with the uterus. Some women have their uteruses removed through a hysterectomy, and some of these procedures result in the presence of a cervical stump CS connected to the vagina V as illustrated. The head 26 is configured to accommodate the presence of either a cervix or the cervical stump CS.

The bladder B communicates with the urethra U and is located anterior to the vagina V and posterior to the pubic bone PB. The digestive tract and the rectum are located posterior to the vagina V. The sacrum S and the coccyx C are located posterior to the digestive tract. The abdominal wall AB protects and supports the internal organs.

During a laparoscopic surgical procedure, one or more access ports are formed through the abdominal wall AB (usually supported by a trocar) to allow a visualization camera and tools to access the internal organs. In the illustrated embodiment, a first trocar 410 provides an access port for surgical tools and a second trocar 412 provides an access port for an optical camera 414. One or more additional ports (for example a nitrogen inflation port) may be provided through the abdominal wall AB in what is traditionally described as a trans-abdominal approach to the vagina V.

Figure 8:
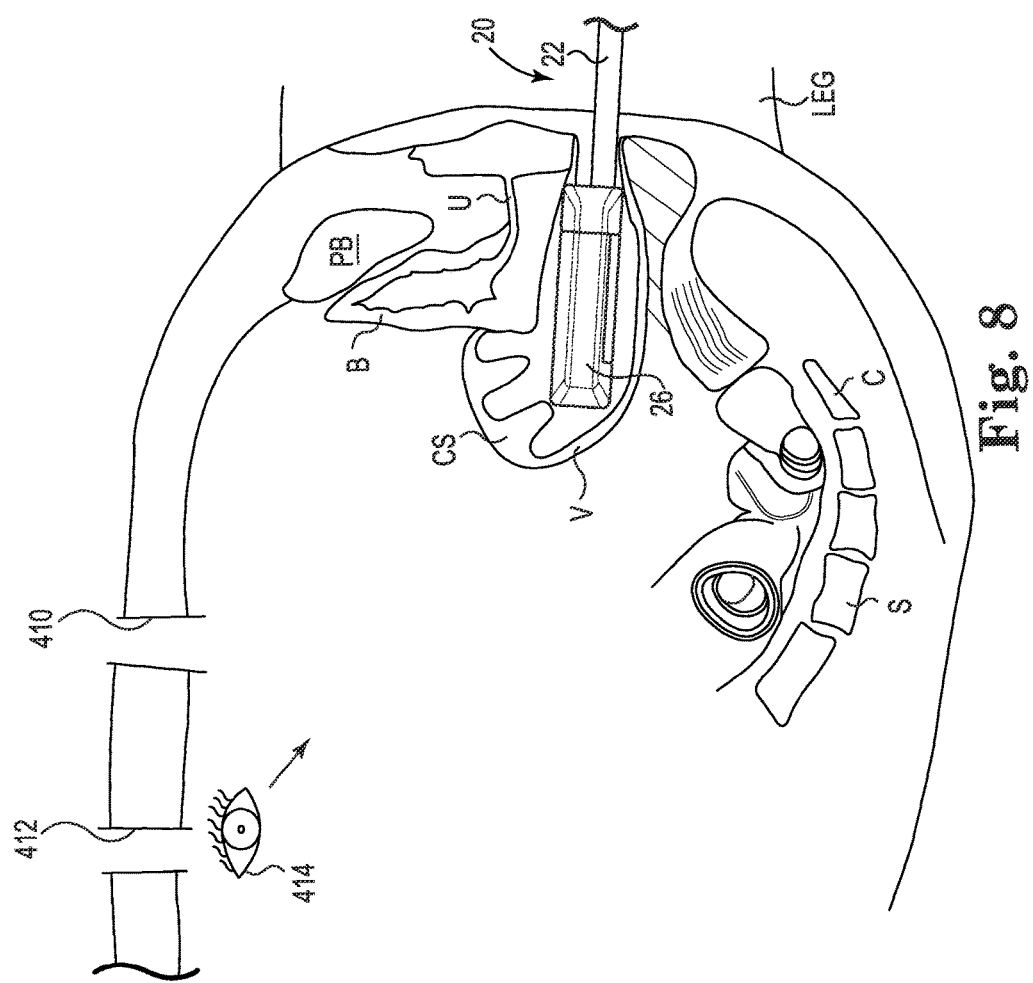
FIG. 8 is a schematic view of the vaginal manipulator illustrated in FIG. 7 inserted into a vagina.
Figure 12:
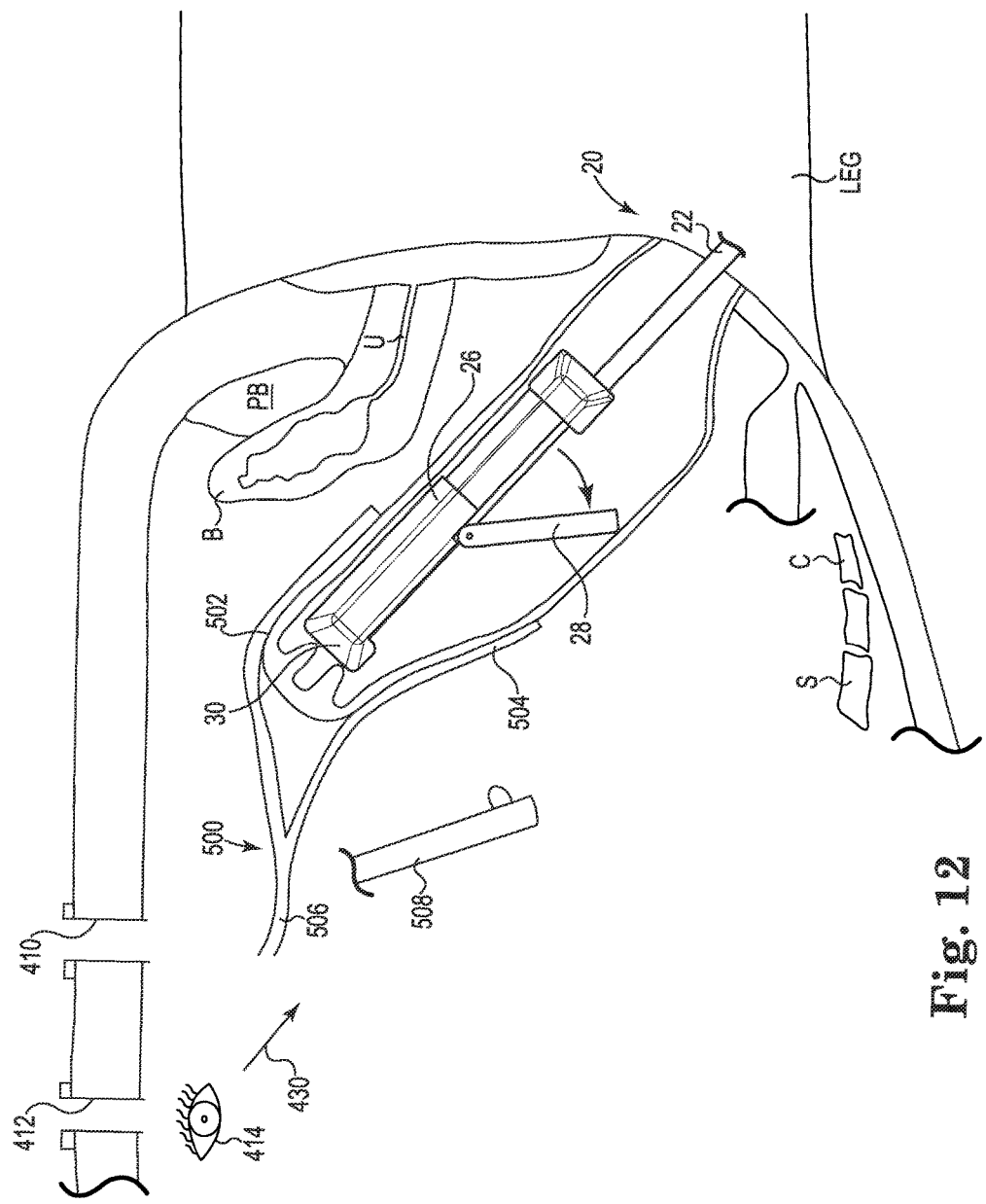
FIG. 12 is a schematic view of the vaginal manipulator illustrated in FIG. 7 employed to attach a support to the vagina in a sacrocolpopexy procedure.

FIG. 8 is a schematic view of the head 26 of the manipulator 20 inserted into the vagina V. The shaft 22 is operable to allow the surgeon to manipulate the head 26 to control the orientation of the vagina V, which is useful when dissecting tissues away from the vagina V (FIG. 7) or when attaching support material to the vagina V (FIG. 12). In some embodiments, the shaft 22 is rigid and allows the surgeon to use the shaft 22 as a lever to move and orient the vagina V to assist in tissue dissection or in presenting a wall of the vagina V for visualization by the camera 414. Movement and use of the manipulator 20 is assisted by the camera 414.

Figure 9:
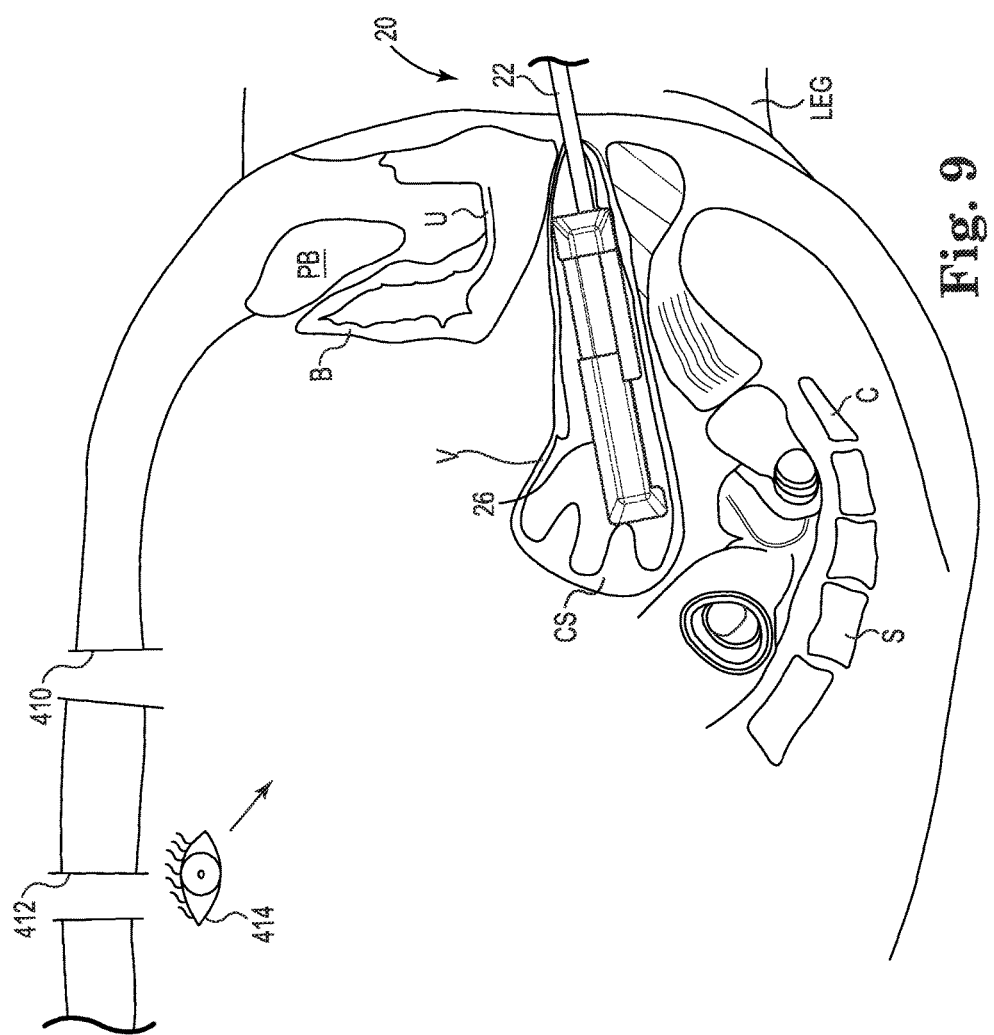
FIG. 9 is a schematic view of the vaginal manipulator illustrated in FIG. 7 assisting in the dissection of vesicovaginal tissue.

FIG. 9 is a schematic view of the manipulator 20 employed to dissect vesico-vaginal tissue away from a wall of the vagina V. One or more surgical tools are inserted through the trocar 410 toward the vagina V. The surgeon moves the head 26 of the device as controlled by the shaft 22 to displace portions of an anterior wall of the vagina V, which allows the surgeon to progressively dissect the vesico-vaginal tissue from between the bladder B and the vagina V. It is desirable to expose the anterior wall of the vagina V to allow the surgeon to optimally orient the vagina V when addressing prolapse and in improving support provided to the vagina V, for example during a sacrocolpopexy procedure. The sleeve 46 of the head 26 of the manipulator 20 can be selectively extended by the surgeon to optimally orient the vagina V for the desired viewing angle.

The sleeve 46 is moved into a forward distal position and indicates a distance to the surgeon as to how far back (or proximal) that tissue should be dissected off of the outer wall of the vagina from the vagina apex or cervical stump CS. In addition, the biased index features 380 function to indicate to the surgeon the length of the sleeve 46 that has been deployed, which indicates an identifiable (measured) landmark distance away from the apex of the vagina.

The sliding feature 46 of the head 26 allows the surgeon to dissect anterior tissue of the vagina V while using the elongated and exposed portion of the head 26 as a backboard for the anterior tissue. The movable sleeve 46 permits full extension of the vagina V by imparting force to the apical area of the vagina V. For some patients, extension of the apex of the vagina V might result in some of the anterior tissue being located proximally beyond the head 26, and thus unsupported. The movable sleeve 46 increases the length of the head 26 to ensure that the anterior tissue is supported internally by the head 26.

Figure 10:
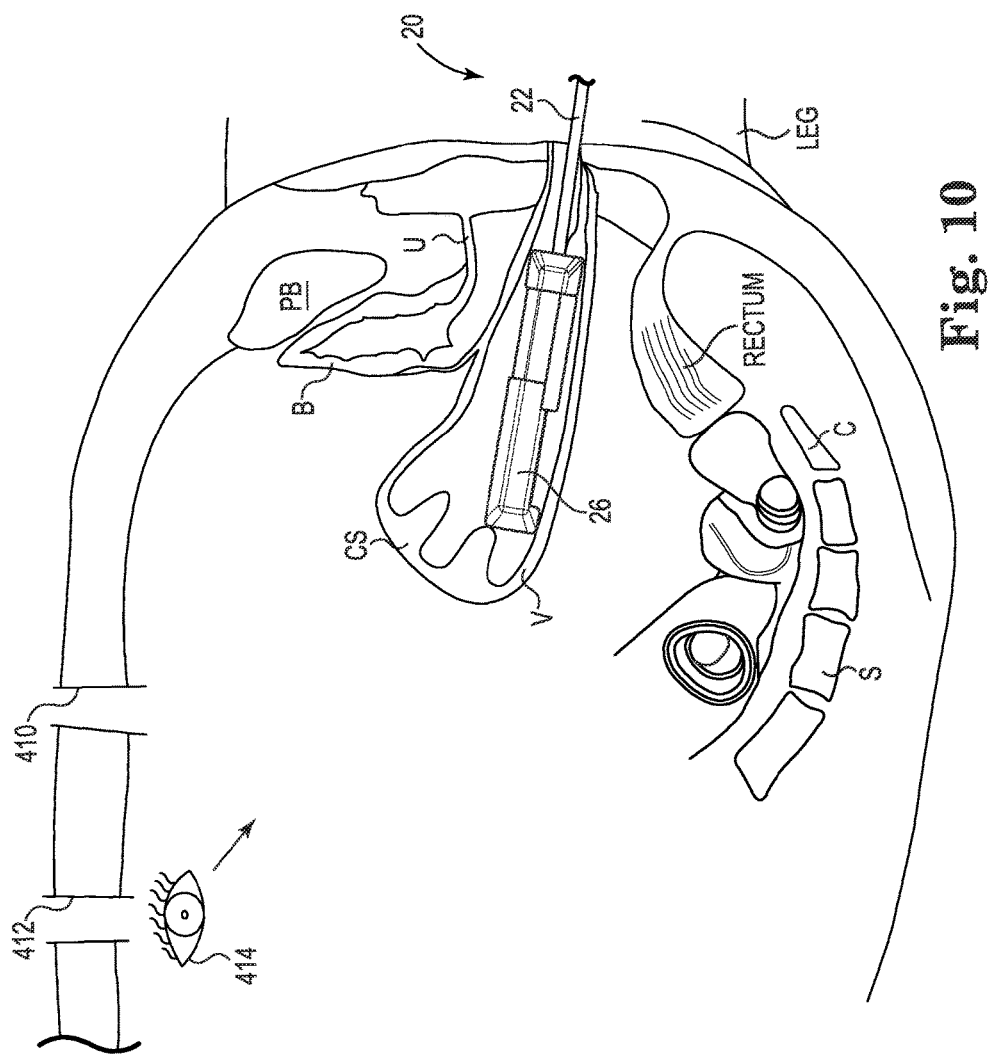
FIG. 10 is a schematic view of the vaginal manipulator illustrated in FIG. 7 assisting in the dissection of rectovaginal tissue.

FIG. 10 is a schematic view of the manipulator 20 employed to dissect recto-vaginal tissue away from a wall of the vagina V. The surgeon employs the shaft 22 to provide a lifting force to the vagina V as suitable other tools are employed to dissect the recto-vaginal tissue from between a posterior wall PW of the vagina V and a sheath or other tissue layers attached to the rectum. Although not shown, the manipulator 20 is also useful for manipulating the vagina V to allow the surgeon to relieve the uterosacral ligament and to access and relieve other connective tissues attached between the vagina V and other organs.

In one embodiment, the recto-vaginal tissue is dissected away from the posterior wall of the vagina V to the same extent as the vesico-vaginal tissue was removed from the anterior wall of the vagina V, which as noted above can be assisted through by the sliding sleeve 46 of the head 26.

Figure 11:
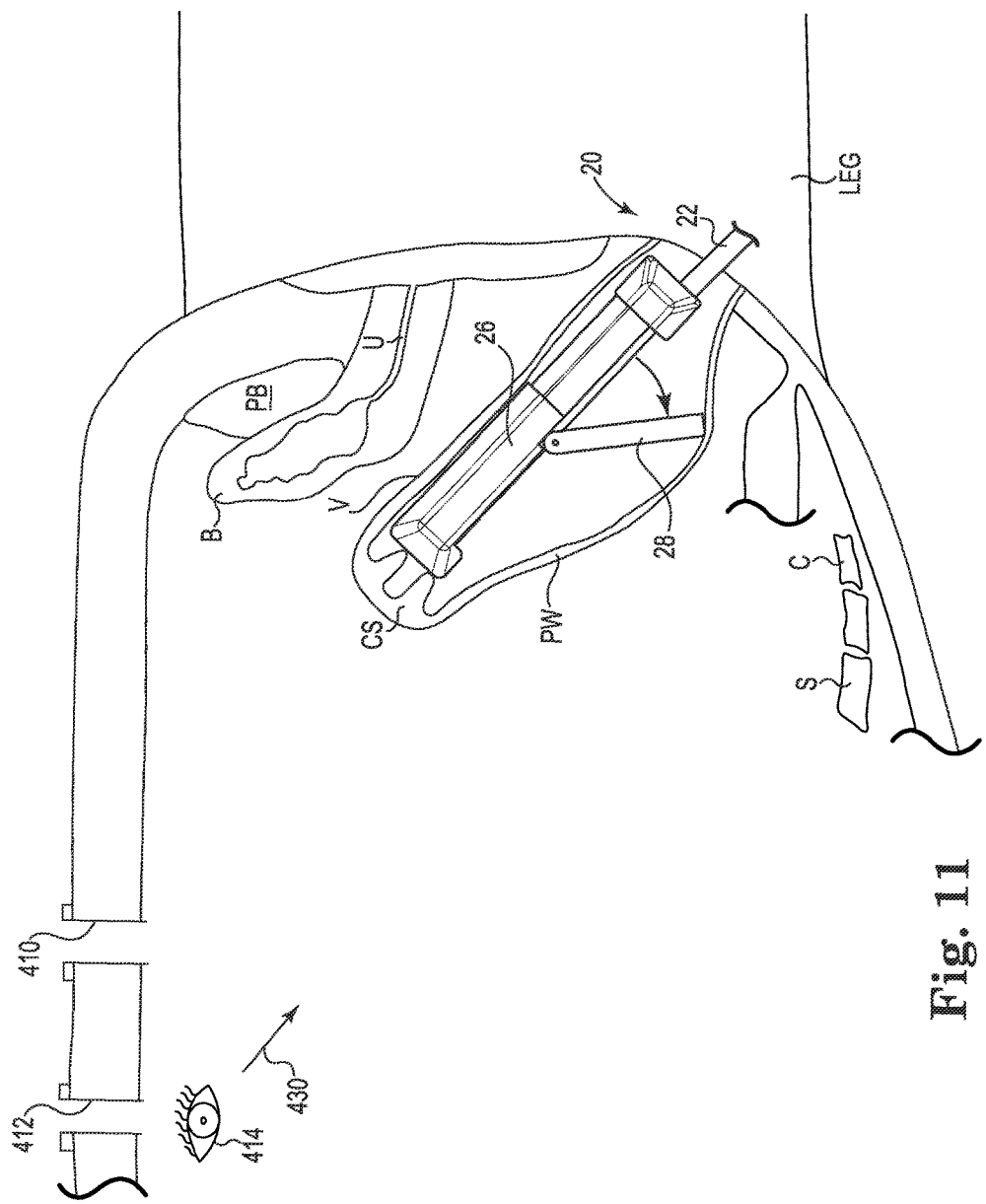
FIG. 11 is a schematic view of the door of the vaginal manipulator illustrated in FIG. 7 deployed to provide a view of a posterior wall of the vagina.

FIG. 11 is a schematic view of the vagina after the anterior wall and the posterior wall PW of the vagina V have been separated from the bladder/rectal connective tissue, respectively. The pocket 94 (FIG. 2) formed in the distal end 50 of the head 26 is engaged with the cervical stump CS.

The posterior wall PW of the vagina V, and in particular, the distal posterior wall PW of the vagina V in the direction of the vaginal opening, is typically impeded by other tissues and hidden from the view of the surgeon during laparoscopic surgery. Some tools, such as the uterine manipulator marketed as the RUMI® II System available from Cooper Surgical of Trumbull, Conn., provide a static device that is insertable into the vagina and/or the uterus. Such tools do not provide a view of the distal posterior wall PW of the vagina V.

In contrast, the kick-out door 28 of the head 26 operates to provide a fully visible view of all portions of the posterior wall PW of the vagina V. In the illustrated embodiment, the door 28 has been pivoted away from the head 26 to move (or "kick out") the posterior wall PW of the vagina V into the line of sight 430 of the camera 414 that is positioned trans-abdominally. The door 28 of the head 26 is moved according to the input from the surgeon to allow the surgeon to advantageously position the posterior wall PW of the vagina V into full visual sight of the camera 414.

FIG. 12 is a schematic view of the manipulator 20 employed to attach a support 500 to the vagina V in a laparoscopically-assisted sacrocolpopexy procedure. One suitable support 500 is a Y-shaped sacrocolpopexy support fabric identified as Restorelle™ available from Coloplast Corp., Minneapolis, Minn. having leg portions 502, 504 diverging away from a tail portion 506.

The patient is prepared for surgery and is usually supine. The access ports are formed in the abdominal wall AB and supported by the trocars 410, 412. The head 26 of the manipulator 20 is inserted into the vagina V to assist in dissecting the vesico-vaginal and recto-vaginal tissues away from the walls of the vagina V as described above.

The door 28 is movable to orient the posterior wall PW of the vagina V into the view of the camera 414, which assists the surgeon in attaching the second leg portion 504 of the support 500 to the posterior wall PW of the vagina, for example through the use of the suture tool 508. The head 26 and the movable sleeve 46 are useful in orienting the vagina V into a desired support-position as the tail 506 of the support 500 is secured to the sacrum S. The attachment of the support 500 to the vagina V supports and surgically corrects the prolapse of the vagina V, or suitably positions the vagina V into a desired anatomical position after removal of the uterus.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. A vaginal manipulator having an adjustable length vaginal probe, the vaginal manipulator comprising:
   a shaft;
   a head having an anterior side opposite a posterior side and including a core fixed to the shaft and a sleeve coupled in a sliding relationship to the core; and
   a door having a distal end that is hinged to the sleeve and a proximal end that is movable away from the core of the head;
   wherein a proximal end of the core defines a proximal end of the head and a distal end of the sleeve defines a distal end of the head, with the proximal end of the core fixed to the shaft;
   wherein the core includes a ramp and a recess that is sized to receive a portion of the door, with the ramp and the recess formed such that a distal portion of the core is thicker than a proximal portion of the core;
   wherein the door includes an inclined surface that is formed such that the distal end of the door is thinner than the proximal end of the door; and
   wherein the door is movable independently from the sleeve.

2. The vaginal manipulator of claim 1, wherein the ramp of the core displaces the proximal end of the door away from the core when the sleeve is moved in a distal direction.

3. The vaginal manipulator of claim 1, further comprising an index coupled in a biased relationship with the core.

4. The vaginal manipulator of claim 3, wherein the index has a first position retained between the core and the sleeve and a second position in which the index is biased to an extended position projecting away from the anterior side of the head when the sleeve is moved away from the proximal end of the core.

5. The vaginal manipulator of claim 1, further comprising an actuator mechanism coupled to the sleeve with the door coupled to the sleeve such that the door moves away from the core when the sleeve is moved in a distal direction by the actuator mechanism.

6. The vaginal manipulator of claim 1, further comprising a handle connected to a proximal end of the shaft.

7. The vaginal manipulator of claim 1, wherein the distal end of the sleeve is movable away from the proximal end of the core to extend a length of the head.

8. The vaginal manipulator of claim 1, wherein the head has a head width extending between parallel lateral sides of the head and a head thickness extending between the anterior side and the posterior side of the head, and the head width is greater than the head thickness.

9. The vaginal manipulator of claim 1, comprising a plurality of indexes coupled to the core and the plurality of indexes are aligned on a central longitudinal axis of the head.

10. The vaginal manipulator of claim 1, wherein the core provides a first anterior side portion of the head and the sleeve provides a second anterior side portion of the head, and the distal end of the sleeve is movable away from the proximal end of the core to extend a length of the anterior side of the head.

11. A vaginal manipulator having an adjustable length vaginal probe, the vaginal manipulator comprising:
   a shaft;
   a head having an anterior side opposite a posterior side and including a core fixed to the shaft and a sleeve coupled in a sliding relationship to the core; and
   a door having a distal end that is hinged to the sleeve and a proximal end that is movable away from the core of the head;
   wherein a proximal end of the core defines a proximal end of the head and a distal end of the sleeve defines a distal end of the head, with the proximal end of the core fixed to the shaft;
   wherein the core includes a ramp and a recess that is sized to receive a portion of the door, with the ramp and the recess formed such that a distal portion of the core is thicker than a proximal portion of the core;
   wherein the door includes an inclined surface that is formed such that the distal end of the door is thinner than the proximal end of the door; and
   wherein the ramp of the core displaces the proximal end of the door away from the core when the sleeve is moved in a distal direction.

12. A vaginal manipulator having an adjustable length vaginal probe, the vaginal manipulator comprising:
   a shaft;
   a head having an anterior side opposite a posterior side and including a core fixed to the shaft and a sleeve coupled in a sliding relationship to the core; and
   a door having a distal end that is hinged to the sleeve and a proximal end that is movable away from the core of the head;
   wherein a proximal end of the core defines a proximal end of the head and a distal end of the sleeve defines a distal end of the head, with the proximal end of the core fixed to the shaft;
   wherein the core includes a ramp and a recess that is sized to receive a portion of the door, with the ramp and the recess formed such that a distal portion of the core is thicker than a proximal portion of the core;
   wherein the door includes an inclined surface that is formed such that the distal end of the door is thinner than the proximal end of the door; and
   wherein the core provides a first anterior side portion of the head and the sleeve provides a second anterior side portion of the head, and the distal end of the sleeve is movable away from the proximal end of the core to extend a length of the anterior side of the head.

* * * * *